United States Patent [19]
Kuznicki et al.

[11] Patent Number: 5,464,619
[45] Date of Patent: Nov. 7, 1995

[54] BEVERAGE COMPOSITIONS CONTAINING GREEN TEA SOLIDS, ELECTROLYTES AND CARBOHYDRATES TO PROVIDE IMPROVED CELLULAR HYDRATION AND DRINKABILITY

[75] Inventors: James T. Kuznicki; Lana S. Turner, both of Cincinnati, Ohio

[73] Assignee: The Procter & Gamble Company, Cincinnati, Ohio

[21] Appl. No.: 253,646

[22] Filed: Jun. 3, 1994

[51] Int. Cl.⁶ .......................... A61K 35/78; A61K 33/14; A61K 9/08
[52] U.S. Cl. .................. 424/195.1; 424/677; 424/678; 424/679; 424/680
[58] Field of Search ................. 424/677–680, 424/195.1

[56] References Cited

U.S. PATENT DOCUMENTS

| | | | |
|---|---|---|---|
| 3,657,424 | 4/1972 | Aktins et al. | 424/153 |
| 3,949,098 | 4/1976 | Bangert | 426/324 |
| 3,950,547 | 4/1976 | Lamar, III et al. | 426/74 |
| 4,042,684 | 8/1977 | Kahm | 424/153 |
| 4,322,407 | 3/1982 | Ko | 424/128 |
| 4,351,735 | 9/1982 | Buddemeyer et al. | 252/1 |
| 4,853,237 | 8/1989 | Prinkkilä et al. | 426/590 |
| 4,874,606 | 10/1989 | Boyle et al. | 426/74 |
| 4,935,256 | 6/1990 | Tsai | 426/330.3 |
| 4,946,701 | 8/1990 | Tsai et al. | 426/597 |
| 5,114,723 | 5/1992 | Stray-Gundersen | 426/74 |
| 5,147,650 | 9/1992 | Fregly et al. | 424/439 |

FOREIGN PATENT DOCUMENTS

| | | |
|---|---|---|
| 82214/82 | 10/1983 | Australia . |
| 202106 | 11/1986 | European Pat. Off. . |
| 264919 | 1/1992 | European Pat. Off. . |
| 464919 | 1/1992 | European Pat. Off. . |
| 4111040 | 6/1992 | Germany . |
| 59-203481 | 11/1984 | Japan . |
| 1060360 | 3/1989 | Japan . |
| 523687 | 4/1976 | U.S.S.R. . |
| 1262235 | 2/1972 | United Kingdom . |
| 91/09538 | 7/1991 | WIPO . |

OTHER PUBLICATIONS

M. L. Riedesel et al.; *Hyperhydration with glycerol solutions;* The American Physiological Society; 1987; pp. 2262–2268.
Abstracts of Shiraimatsu Shinyaku JP 63160567 (Jul. 4, 1988).
Mitsui Norinkk(II) JP 01233277 (Sep. 19, 1989).
Abstracts of Norink(I) JP 02223519 (Sep. 5, 1990).

*Primary Examiner*—Shep K. Rose
*Attorney, Agent, or Firm*—Rose Ann Dabek; J. C. Rasser

[57] ABSTRACT

This invention relates to a composition, preferably in the form of a beverage, whereby cellular hydration and drinkability are enhanced by the combination of green tea solids with selected levels and types of electrolytes and carbohydrates. The compositions comprise (a) from about 0.01% to about 0.35% flavanols; (b) from about 0.01% to about 0.3% sodium ions; (c) from about 0.005% to about 0.08% potassium ions; (d) from about 0.1% to about 20% of a carbohydrate which provides; (i) from about 0.05% to about 10.0% fructose; (ii) from about 0.05% to about 10.0% glucose; and (e) water.

19 Claims, No Drawings

BEVERAGE COMPOSITIONS CONTAINING GREEN TEA SOLIDS, ELECTROLYTES AND CARBOHYDRATES TO PROVIDE IMPROVED CELLULAR HYDRATION AND DRINKABILITY

FIELD OF INVENTION

This invention relates to a composition, preferably in the form of a beverage, whereby cellular hydration and drinkability are enhanced by the combination of green tea solids with selected levels and types of electrolytes and carbohydrates.

BACKGROUND OF THE INVENTION

Moderate physical activity, prolonged exercise or working in hot, humid environments causes excessive loss of minerals and body fluids through perspiration and breathing. Physical activity, such as exercise, particularly in the heat, places a great metabolic demand on a human body. Heat generated during exercise is dissipated during sweating.

Sweat which is lost from the body during exercise can produce a state of dehydration or hypohydration. Associated with dehydration is an impairment of the body's heat dissipation and performance capacity. It is well known that loss of water, electrolytes, and depletion of carbohydrates are the primary causes of fatigue which can impair work capacity. To maintain performance it is necessary to replace the lost water, electrolytes, carbohydrates and other nutrients.

Attempts have been made to counteract these adverse effects of strenuous activity. Consumption of water helps maintain body temperature and blood volume, but water is absorbed relatively slowly. Products have been developed recently which combine sugar, water, essential electrolytes and other ingredients lost from the body through physical activity. Several well known products are Gatorade Thirst Quencher®, All Sport® and PowerAde®. Other compositions are well known and are described, for example in U.S. Pat. No. 4,874,606 issued to Boyle et al. Oct. 17, 1989 and 4,322,407 issued to Ko, Mar. 30, 1982.

The focus of rehydration (Sports) beverages, has been to replenish lost electrolytes, carbohydrates, and other essential constituents which are lost through dehydration. Only a few address the unmet need of providing rapid cellular hydration and water distribution within the body. Beverage formulas that address cellular needs are described, for example, in U.S. Pat. No. 5,147,650 to Fregly issued Sep. 15, 1992 and 5,114,723 issued to Stray-Gundersen May 19, 1992.

Although there are formulas that help to combat some of the unmet needs, many of the commercial beverages cause a feeling of fullness or satisfaction and therefore drinking is stopped before the amount of liquid needed for rehydration is consumed.

The invention described herein is a novel composition which surprisingly provides enhanced cellular hydration while avoiding the premature cessation of drinking. Further, users of the product report lower levels of fatigue, and increased cognitive performance after heat dehydration when the novel composition is used.

An object of the present invention is to provide beverage compositions which facilitate the distribution of fluid throughout the body, particularly at the cellular level.

Another object of this invention is to provide thirst quenching beverage compositions.

Still another object of the present invention is to provide beverage compositions with increased drinkability.

These and other objects will become apparent from the following detailed description.

All percentages herein are by weight unless otherwise specified.

SUMMARY OF THE INVENTION

The subject invention relates to a liquid composition comprising:
(a) from about 0.01% to about 0.35% flavanols;
(b) from about 0.01% to about 0.3% sodium ions;
(c) from about 0.005% to about 0.08% potassium ions;
(d) from about 0.1% to about 20% of a carbohydrate which provides
  (i) from about 0.05% to about 10.0% fructose;
  (ii) from about 0.05% to about 10.0% glucose; and
(e) water.

A dry composition comprising:
(a) from about 0.1% to about 3.5% flavanols;
from about 0.1% to about 3.0% sodium ions;
(c) from about 0.05% to about 0.8% potassium ions;
(d) from about 1.0% to about 95% of a carbohydrate which provides
  (i) from about 0.5% to about 50% fructose;
  (ii) from about 0.5% to about 50% glucose.

A method of rapidly rehydrating human or animal cells which have been dehydrated through loss of water and minerals by the ingestion of these compositions is also described. This product can be administered as a powder or as a tablet.

DETAILED DESCRIPTION

Definitions

As used herein, the term "comprising" means various components can be conjointly employed in the beverages of this invention. Accordingly, the terms "consisting essentially of" and "consisting of" are embodied in the term comprising.

As used herein, the term "drinkability" means the volume of beverage consumed per drinking occasion. Beverages with enhanced drinkability can be consumed in large volumes without a feeling of fullness or satisfaction.

As used herein, the term "thirst quenching" relates to the physiological ability of a beverage to rapidly deliver water through the human digestive system and distribute it throughout the body and into the cells.

As used herein, the term "beverage composition" means a composition that is single strength and ready to drink. As used herein, "beverage concentrate" refers to a concentrate that is in liquid form. The concentrate is usually formulated to provide a drinkable beverage composition when reconstituted or diluted with water. The composition can also be made in an essentially dry mixture form. The essentially dry mixture can be in the form of either a powder or a tablet. These compositions are referred to herein as a "dry composition."

As used herein, the term "tea materials" refers to teas which include materials obtained from the genus Camellia including *Camellia sinensis* and *Camellia assaimica*, for instance, freshly gathered tea leaves, fresh tea leaves that are dried immediately after gathering, fresh tea leaves that have been heat treated before drying to inactivate any enzymes present, unfermented tea, fermented tea, instant green fermented tea, partially fermented tea leaves and aqueous extracts of these leaves. Tea materials are tea leaves, their extracts, tea plant stems and other plant materials which are related. Members of the genus *Phyllanthus, Catechu gambir* or Uncaria family of tea plants can also be used. Mixtures of unfermented, partially fermented and fermented, teas can be used.

As used herein, the term "tea solids" refers to solids extracted from tea materials. The tea materials used in the present composition must contain unoxidized, unpolymerized flavanols.

As used herein, the term "tea extract" refers to an aqueous solution obtained from the extraction of tea materials. This includes the flavanols and caffeine that is present. The term "tea extract" also encompasses aqueous solutions which have been concentrated or dried.

As used herein "flavanols" or "catechins" means primarily catechin, epicatechins, and their derivatives. These derivatives include the sugar salts, sugar esters, and other edible physiologically available derivatives. Green tea solids contain these flavanols. Black tea, fruits, and other natural sources also contain these flavanols but to a lesser degree. The preferred flavanols are catechin, epicatechin, gallocatechin, epigallocatechin, epicatechin gallate, and epigallocatechin gallate.

All percentages herein are by weight unless otherwise specified.

Beverage Composition

The beverage compositions described herein have been shown to improve cognitive performance after, and decrease the recovery time from, dehydration relative to water in individuals subjected to heat-induced dehydration. Specifically, the invention comprises flavanols, which significantly enhances cellular rehydration.

When the beverage compositions of the present invention are administered, the body's physiological response to exercise or environmental exposure is greatly enhanced compared to the response when the body receives no fluids, receives only water, or receives commercial beverages which contain electrolytes and a sugar source in addition to water. The cellular hydration advantage of the novel beverage compositions described can be clearly measured using Multi-frequency Bio-Impedance Spectroscopy.

The replacement of body fluids and electrolytes lost by those individuals engaged in moderate to strenuous activities is essential if smooth and efficient muscle function is to be maintained. Water and electrolytes are lost as the body regulates its temperature through perspiration. Those individuals undergoing work, exercise, or any activity requiring moderate to strenuous use of the muscles and/or the loss of body water and electrolytes need rapid replacement of the lost body fluids and electrolytes.

The beverage compositions of this invention may be consumed by persons engaged in vigorous activity, such as athletes. It may also be consumed by people doing strenuous work, especially in hot environments, or by people who have suffered the loss of body fluids and electrolytes as a result of some illness or disease. The beverage composition of this invention may also be consumed by anyone as a supplement to normal dietetic requirements for energy and/or water.

The beverage compositions of the present invention may be manufactured and sold as a single-strength beverage for direct consumption by the consumer. The product may be in the form of a syrup, an aqueous concentrate, a dry powder, or granules which are diluted with water to yield a beverage which fulfills all the requirements of this invention. Alternatively, the product may be in the form a tablet which can be taken with water.

Flavanols

An important ingredient in the beverage composition of the present invention are the flavanols. The flavanols are natural substances present in a variety of plants (e.g. fruits, vegetables, flowers). The flavanols used in present invention can be extracted from fruit, vegetables, green tea or other natural sources by any suitable method well known to those skilled in the art. For example, extraction with ethyl acetate or chlorinated solvents is one way to isolate flavanols or catechins from green tea; or, they may be prepared by synthetic or other appropriate chemical methods. Flavanols, including catechin, epicatechin, and their derivatives are commercially available.

The flavanols may be extracted from either a single plant or mixtures of plants. The preferred flavanols are obtained by the extraction of plants, e.g. green tea and related plants. Many fruits, vegetables, and flowers contain flavanols but to a lesser degree. Plants containing flavanols are known to those skilled in the art. Examples of the most common flavanols which are obtained from extraction of tea plants and other members of the *Catechu gambir* or (Uncaria family) are catechin, epicatechin, gallocatechin, epigallocatechin, epicatechin gallate, epigallocatechin gallate.

The preferred source of flavanols in the beverage composition of the present invention is green tea. It is believed that the green tea and in particular the flavonols present in green tea when incorporated into the beverage are responsible for the observed enhanced cellular rehydration.

The flavanols may be in the form of a tea extract. The tea extract can be obtained from the extraction of unfermented teas, fermented teas, partially fermented teas and mixtures thereof as long as the unoxidized flavanols come within the specified range. Preferably the tea extracts are obtained from the extraction of unfermented and partially fermented teas. The most preferred tea extracts are obtained from green tea. Both hot and cold extracts can be used in the present invention. Suitable methods for obtaining tea extracts are well known, see, for example, U.S. Pat. Nos. 4,935,256 to Tsai, issued Jun. 1990; 4,680,193 to Lunder, issued Jul. 1987; and 4,668,525 to Creswick, issued May 26, 1987. A particularly preferred method for obtaining a tea extract is described, for example in co-pending application Ser. No. 08/178/702, filed Jan. 10, 1994.

The drinkable beverage of the present invention comprises about 0.01% to about 0.35% unoxidized, unpolymerized flavanols, preferably from about 0.02% to about 0.2%, equally preferred from about 0.025% to about 0.1% and most preferably from about 0.03% to about 0.075% unoxidized, unpolymerized flavanols.

Caffeine

It is preferred that the drinkable beverage contain from about 0.0% to about 0.04% caffeine, preferably about 0.01% to about 0.03%, and most preferably from about 0.013% to about 0.02% caffeine in addition to the unoxidized, unpolymerized flavanols. The total amount of caffeine includes the amount of caffeine naturally present in the tea extract, flavoring agent, and other ingredients as well as any added caffeine.

Electrolytes

Among the major physiological electrolytes are potassium and sodium. The electrolytes and ionic components for the present invention are usually, but not necessarily, obtainable from their corresponding water-soluble and non-toxic salts. They are also present in fruit juices and in the tea extract. Unless otherwise defined, the amount of electrolytes or ionic components in the beverage is based on those present in the final drinkable beverage composition. The electrolyte concentration is of the ion only and not the salt. Some of the less soluble salts must be "solubilized" in water, or in water having an acidic pH, in order to be useful in the present invention.

The potassium ion component can be provided by any salt such as the chloride, carbonate, sulfate, acetate, bicarbonate, citrate, phosphate, hydrogen phosphate, tartrate, sorbate and the like, or mixtures thereof or as a component of added fruit juice or tea. The potassium ions are preferably present in the drinkable beverage composition of the present invention in an amount of at least 0.005% to about 0.08%, preferably from about 0.01% to about 0.06% and most preferably from about 0.02% to about 0.04%.

Likewise, the sodium ion component can be obtained from any readily available sodium salt, such as the chloride, carbonate, bicarbonate, citrate, phosphate, hydrogen phosphate, tartrate, benzoate and the like, and mixtures thereof or as a component of added fruit juice or tea. It is important in the present invention that the sodium concentration be low enough to facilitate the absorption of water by osmosis and not osmotically draw water out of the body into the intestine. The concentration of sodium needed to do this is preferably lower than that of plasma sodium. The sodium ions are present in the drinkable beverage composition of the present invention in an amount of at least 0.01% to about 0.3% preferably in an amount of from about 0.02% to about 0.2%, and more preferably from about 0.04% to about 0.15%.

In addition to potassium and sodium ions, the composition can additionally contain chloride ion from about 0.01% to about 0.10%, preferably from about 0.03% to about 0.1% and most preferably from about 0.05% to about 0.09%. The chloride ion component can be provided by a salt such as sodium chloride or potassium chloride. Other ions such as calcium and magnesium may also be added. These ions may also be provided as a salt. The total level of ions present includes the amount naturally present in the beverage along with any added ion addition. For example, if sodium chloride is added, the amount of sodium ion and amount of chloride ion would be included in the total amount of each ion accordingly.

Carbohydrate

The beverages of the present invention also contains soluble carbohydrates. The carbohydrates can be sweeteners as well as energy sources. In selecting carbohydrates for use in the present beverage it is important that the levels chosen allow a sufficient rate of stomach emptying and intestinal absorption to be effective. The carbohydrate can be a mixture of glucose and fructose or be a carbohydrate which hydrolyzes or otherwise forms glucose and fructose in the digestive track.

As used herein, the term "carbohydrate" refers to monosaccharides, oligosaccharides, complex polysaccharides, or mixtures thereof. The monosaccharides include tetroses, pentoses, hexoses, and ketohexoses. Examples of hexoses are aldohexoses such as glucose, known as grape sugar. The amount of glucose used for the drinkable beverage composition of the present invention preferably is from about 0.05% to about 10%, more preferably from about 1.0% to about 5.0% and most preferably from about 1.5% to about 3%. Fructose, known as fruit sugar, is a ketohexose. Preferably, the amount of fructose present in the drinkable beverage is from about 0.05% to about 10%, preferably from about 1.0% to about 5%, and most preferably from about 1.5% to about 3%. The composition herein must contain these two sugars and/or carbohydrates that form these sugars in the body (i.e. sucrose, maltodextrin, corn syrups, high frutose corn syrups). An important class of carbohydrates is a disaccharide. An example of a disaccharide is sucrose, know as cane sugar or beet sugar. Preferably, the amount of sucrose present in the drinkable beverage composition of the present invention is from about 1% to about 20%, more preferably from about 2.0% to about 10.0%, and most preferably from about 3% to about 6%.

The desired total carbohydrate level is from about 0.1% to about 20%, preferably from about 0.5% to about 15% and most preferably from about 3% to about 6%.

One of the complex carbohydrates usable for the present invention is maltodextrin. Maltodextrins are a form of complex carbohydrate molecule several glucose units in length. They are spray-dried carbohydrate ingredients made by controlled hydrolysis of corn starch. The dextrose equivalence ("D.E.") of maltodextrins provide a good index of the degree of starch polymer hydrolysis. The amount of maltodextrin used in the drinkable beverage composition is 0% to about 10%, preferably from 1% to about 4%. The preferred maltodextrins are those with a DE up to 20.

The preferred carbohydrate of the present invention is comprised of a combination of fructose and glucose to achieve an energy source capable of providing needed fuel values as the demand thereof may vary. Since sucrose is hydrolyzed to fructose and glucose in the digestive tract it can be used as a source of fructose and glucose. Each of these sugars is an energy food fully utilizable by cells of the body.

The total carbohydrates used in the present invention are preferably in the amount of from about 0.1% to about 20% of the total weight of the drinkable beverage composition. The total amount of carbohydrate include any added carbohydrate as well as those naturally present in the fruit juice or tea extract.

A carbohydrate derivative, polyhydric alcohol, such as glycerol may also be used in the present invention to provide a source of sweetness and to provide energy such that it is readily absorbed and distributed throughout the body. However, the presence of glycerol is not essential to achieve the advantages of the present invention. When desired, amounts of from about 0.1% to about 15%, preferably from about 6% to about 10% glycerol can be used in the present invention.

For diet beverages, non-caloric sweeteners can be used in conjunction with at least about 0.1% carbohydrate. Examples of such sweeteners include aspartame, saccharine, cyclamates, acesulfam-K, L-aspartyl-L-phenylalanine lower alkyl ester sweeteners, L-aspartyl-D-alanine amides as disclosed in U.S. Pat. Nos. 4,411,925 to Brennan, et al (1983), L-aspartyl-D-serine amides disclosed in 4,399,163 to Brennan et al (1983), L-aspartyl-hydroxymethyl alkane amide sweeteners disclosed in 4,338,346 issued to Brand (1982), L-aspartyl-1-hydroxyethylalkane amide sweeteners disclosed in 4,423,029 to Rizzi (1983), glycyrrhizins, synthetic alkoxy aromatics, etc. Lo Han Guo juice, stevioside and other natural sources of sweeteners can also be used.

Other Ingredients

Other minor ingredients can be included in the beverages of the present invention. Such ingredients include natural and synthetically prepared flavoring agents, natural and synthetically prepared colors, preservatives, acidulants, gums, emulsifiers, oils and vitamins.

Flavoring Agents

A flavoring agent is recommended for the beverage compositions of this invention in order to enhance the palatability. Any natural or synthetic flavor agent can be used in the present invention. Flavoring agents can be selected from a fruit juice, a fruit flavor, a botanical flavor or mixtures thereof. In particular the combination of tea flavors, preferably green tea or black tea flavors, together with fruit juices has an appealing taste. Preferred juices are apple, pear, lemon, lime, mandarin, grapefruit, cranberry, orange, strawberry, grape, kiwi, pineapple, passion fruit, mango, guava, raspberry and cherry. Citrus juices, preferably grapefruit, orange, lemon, lime, mandarin and juices of mango, passion fruit and guava, or mixtures thereof are most preferred. Preferred natural flavors are jasmine, chamomile, rose hip, peppermint, haw, chrysanthemum, water chestnut, sugar cane, lychee, bamboo shoots and the like.

The fruit juices can be present as the base to which the flavanols and other ingredients are added or used as the flavoring agent. When used as the flavoring agent, the fruit juice is present in an amount of from about 0.5% to about 50%, and more preferably from about 5.0% to about 30%, by weight of the beverage. This concentration is based on the single strength of the beverage.

Fruit flavors, botanical flavors, tea flavors and mixtures thereof can also be used as the flavoring agent. Particularly preferred fruit flavors are the citrus flavors including orange flavors, lemon flavors, lime flavors and grapefruit flavors. Besides citrus flavors, a variety of other fruit flavors can be used such as apple flavors, grape flavors, raspberry flavors, cranberry flavors, cherry flavors, pineapple flavors and the like. These fruit flavors can be derived from natural sources such as fruit juices and flavor oils, or else be synthetically prepared.

The flavor agent can also comprise a blend of various flavors e.g. lemon and lime flavors, citrus flavors and selected spices (the typical cola soft drink flavor) etc. If desired the flavor in the flavoring agent may be formed into emulsion droplets which are then dispersed in the beverage drink. Because these droplets usually have a specific gravity less than that of water and would therefore form a separate phase, weighting agents (which can also act as clouding agents) can be used to keep the emulsion droplets dispersed in the beverage. Examples of such weighting agents are brominated vegetable oils (BVO) and resin esters, in particular the ester gums. See L. F. Green, Developments in Soft Drinks Technology, Vol. 1 (Applied Science Publishers Ltd. 1978) pp. 87–93 for a further description of the use of weighting and clouding agents in liquid beverages. Typically the flavoring agents are conventionally available as concentrates or extracts or in the form of synthetically produced flavoring esters, alcohols, aldehydes, terpenes, sesquiterpenes, and the like. Typically, such flavoring agents are added in quantities in the amount of from about 0.001% to about 2%, preferably from about 0.02% to about 0.09%, by weight of the beverage.

Colors

If desired, coloring agents can also be added into the drinkable beverage compositions or beverage concentrates of the present invention. Any soluble coloring agents approved for food use can be utilized for the present invention.

Preservatives

When desired, preservatives, such as sorbic acid, benzoic acid, hexametaphosphate and salts thereof, can be added into the drinkable beverage composition or beverage concentrate of the present invention.

Acidulant

Also, if desired, the composition can contain an acidulant. This is intended to describe edible acids such as malic, citric, tartaric, fumaric and the like which are commonly used in beverage drinks. An amount of an acidulant may be used to maintain a pH of less than 4.6. Preferably the beverage has a pH of from about 2.5 to about 4.0. This will enable the beverage to remain microbially safe.

Organic as well as inorganic edible acids may be used to adjust the pH of the beverage. The acids can be present in their undissociated form or else as their respective salts, for example, potassium or sodium hydrogen phosphate, potassium or sodium dihydrogen phosphate salts. The preferred acids are edible organic acids which include citric acid, malic acid, fumaric acid, adipic acid, phosphoric acid, gluconic acid, tartaric acid, ascorbic acid, acetic acid, phosphoric acid or mixtures thereof. The most preferred acids are citric and malic acids.

The acidulant can also serve as an antioxidant to stabilize beverage components. Examples of commonly used antioxidant include but are not limited to ascorbic acid, EDTA ethylenediaminetetraacetic acid) and salts thereof.

Gums, Emulsifiers, Oils

Gums, emulsifiers and oils can also be included in the beverage for texture and opacity purposes. Typical ingredients include guar gum, xanthan gum, alginates, carboxymethylcellulose (CMC), mono-di glycerides, lecithin, starches, pectin, pulp, cotton seed oil and vegetable oil.

Vitamins

The beverage compositions can additionally comprise from 0% to about 150% of the U.S. RDA of vitamins such that the vitamins are chemically and physically compatible with the essential elements of the beverage composition. Preferably Vitamins A, C, and E are added. Other vitamins such as D and B may also be added.

Minerals

Additional minerals can be added to the beverage or dry compositions of the present invention. The compositions can comprise from 0% to about 150% of the U.S. RDA of minerals such that the minerals are chemically and physically compatible with the function and essential elements of the present invention. Preferred minerals are calcium, chromium, copper, fluorine, iodine, iron, magnesium, manganese, phosphorus, selenium, silicon, molybdenum and zinc. Particularly preferred minerals are magnesium, phosphorus, and iron.

BEVERAGE PREPARATION

The drinkable beverage composition may be prepared by mixing together all of the ingredients. The mixture is dissolved in water and agitated with a mechanical stirrer until all of the ingredients have gone into solution. The preservative, if used, can then be added. The mixture can then be adjusted to a desired pH with an acidulant.

Single strength fruit juice may also be used to prepare the beverage compositions of the present invention. The fruit juice or fruit juice concentrate can be used as the liquid base to which the flavanols and electrolytes are added. Any carbohydrates, water, electrolytes etc. present in the fruit juice or fruit juice concentrates are included in the total amount claimed herein.

In making a single strength beverage, a beverage concentrate syrup can be formed first. One way to prepare the concentrate form of the liquid beverage would be to start with less than the required volume of water that is used in the preparation of the drinkable beverage composition. Another way would be to partially dehydrate the finally prepared drinkable beverage composition to remove only a portion of the water and any other volatile liquids present. Dehydration can be accomplished in accordance with well known procedure, such as evaporation under vacuum. The concentrate can be in the form of a relatively thick, syrupy liquid. The syrup is typically formed by adding suitable (i.e. sugar, electrolytes, emulsions) to the beverage concentrate. The syrup is then mixed with water to form a finished beverage or finished beverage concentrate. The weight ratio of water:syrup is typically from about 2:1 (3×syrup) to about 5:1 (6×syrup).

The solid can be in the form of an essentially dry powder or a tablet. The dry form can later be reconstituted with a proper amount of water to make the final drinkable beverage composition or taken with the appropriate amount of water to deliver the levels of ingredients stated herein.

Carbon dioxide can be introduced either into the water to be mixed with the beverage concentrate, or into the drinkable beverage composition, to achieve carbonation. The carbonated beverage composition can then be stored in a suitable container and then sealed. See L.F. Green, Developments in Soft Drinks Technology, Vol. 1 (Applied Science Publishers Ltd. 1978), pp. 102–107, for a further description of beverage making, in particular the process for carbonation.

Dry Mixture

The essentially dry mixture of the beverage composition can be prepared by blending the proper amounts and ratios of all the required dry ingredients together. Alternatively, the finally prepared drinkable beverage composition can be dehydrated to give the essentially dry mixture of the beverage composition. The essentially dry mixture, either as a powder, granules or tablets, can later be dissolved in a proper amount of water, carbonated or non-carbonated, to make the final drinkable beverage or taken in conjunction with water.

Essentially dry forms include tablets, capsules, granules and bulk powders. Tablets may contain suitable binders, lubricants, diluents, disintegrating agents, coloring agents, flavoring agents, flow-inducing agents and melting agents. Suitable carriers and excipients that may be used to formulate dry forms of the present invention are described in U.S. Pat. No. 3,903,297, Rober, issued Sep. 2, 1975. Techniques and compositions for making dry forms useful in the methods of this invention are described in the following references; 7 *Modern Pharmaceutics*, Chapters 9 and 10 (Banker & Rodes, editors, 1979); Liberman et al.; *Pharmaceutical Dosage Forms: Tablets* (1981); and Ansel, Introduction to *Pharmaceutical Dosage Forms*, 2nd Edition (1976).

A typical dry powder comprises from about 0.1% to about 3.5% flavanols, from about 0.1% to about 3.0% sodium ions, from about 0.05% to about 0.8% potassium ions, from about 0.5% to about 50% fructose, and from about 0.5% to about 50% glucose. If desired from about 1% to about 95% sucrose can be used instead of fructose and glucose since sucrose is hydrolyzed to fructose and glucose in the body. The actual concentration of the ingredients in the dry powder will depend upon the amount of dilution or the amount of water consumed.

The following examples are given to illustrate the invention and are not intended to limit it in any way.

EXAMPLE I

A drinkable beverage composition is prepared by combining the following ingredients:

| Ingredients | Wt. % |
| --- | --- |
| Fruit Juice Concentrate | 4.0 |
| *Green Tea Solids | 0.35 |
| Flavoring | 0.06 |
| Sodium Citrate | 0.32 |
| Ascorbic Acid | 0.01 |
| Aspartame | 0.01 |
| Glucose | 0.8 |
| Water | 94.45 |

*The green tea solids contain about 8% caffeine and about 29% unoxidized flavanols. The final drinkable beverage has about 0.0275% caffeine and about 0.097% unoxidized flavanols.

EXAMPLE II

A beverage composition is prepared by blending the following ingredients:

| Ingredients | Wt. % |
| --- | --- |
| Fruit Juice | 1.7 |
| Juice Concentrate | 0.64 |
| *Green Tea Extract | 63 |
| Lemon Lime Flavoring | 0.3 |
| Aspartame | 0.25 |
| Ascorbic Acid | 0.1 |
| Sodium Chloride | 0.035 |
| Colorant | 0.1 |
| Sodium Citrate | 0.4 |
| Emulsion | 1.6 |
| Water | 31.875 |

*The green tea extract contains about 0.56% solids, about 0.04% caffeine and about 0.156% unoxidized flavanols. The final drinkable beverage has about 0.025% caffeine and about 0.098% unoxidized flavanols.

EXAMPLE III

A healthy person who is exposed to temperatures of about 105° F. at 75% humidity for about one hour can consume 835 cc's of a beverage prepared according to Example 1. The expansion of the intra-cellular compartment can be measured using Multi-frequency Bio-Impedance Spectroscopy with a Xitron 4000b spectrometer (Xitron Technologies, Inc.). Measurements of this kind show that the composition of the invention is able to significantly expand the intracellular water compartment when compared to commercial beverages containing carbohydrates and electrolytes. The expansion may typically become noticeable when the actual volume consumed is about equal to the amount the person would lose through perspiration during heat exposure. The difference is statistically significant ($p=0.051$).

| EXPANSION OF THE INTRA-CELLULAR WATER COMPARTMENT | |
| --- | --- |
| Beverage prepared according to Example 1 | Commercial beverage containing electrolytes and carbohydrates |
| N = 8 | N = 9 |
| 646 ± 212 cc | 28 ± 200 cc |

N is number of subjects.

EXAMPLE IV

Five human volunteer subjects, each of whom exercises regularly by running a constant distance per day (5–8 k), are provided one of four separate beverages at the completion of their usual daily run for four days in a row. The beverages are the beverage prepared according to Example II, water, commercial carbohydrate-electrolyte beverage 1 (CE-1), or commercial carbohydrate electrolyte beverage 2 (CE-2). The order of beverage consumption is randomized separately for each subject. The subject is allowed to drink as much of each beverage as they wish for 30 minutes after exercise. All beverages are lime flavor except water. The beverage according to Example II is consumed in a greater volume than water and both of the CE beverages.

| AVERAGE BEVERAGE VOLUME CONSUMPTION (CC's) AFTER EXERCISE | | | |
| --- | --- | --- | --- |
| *EXAMPLE II BEVERAGE | CE-1 | CE-2 | WATER |
| 1269 cc | 1099 cc | 977 cc | 894 cc |
| 100% | 87% | 77% | 70% |

*Preferred beverage is expressed as 100% consumption (1269 cc). Beverages CE-1, CE-2 and water are expressed as a percentages of that volume.

What is claimed:

1. A dry composition consisting essentially of:
   (a) from about 0.1% to about 3.5% flavanols;
   (b) from about 0.1% to about 3% sodium ions;
   (c) from about 0.05% to about 0.8% potassium ions;
   (d) from about 1.0% to about 95% of a carbohydrate which provides
      (i) from about 0.5% to about 50% fructose; and
      (ii) from about 0.5% to about 50% glucose.

2. The composition according to claim 1 wherein said composition is in the form of a tablet.

3. The concentrate wherein said concentrate is in the form of a syrup consisting essentially of;
   (a) from about 0.03% to about 2.1% flavanols;
   (b) from about 0.03% to about 1.8% sodium ions;
   (c) from about 0.015% to about 0.48% potassium ions;
   (d) from about 0.3% to about 70% of a carbohydrate which provides
      (i) from about 0.15% to about 50.0% fructose;
      (ii) from about 0.15% to about 50.0% glucose; and
   (e) from about 30% to about 70% water.

4. A fluid composition for providing enhanced cellular hydration and drinkability consisting essentially of:
   (a) from about 0.01% to about 0.35% flavanols;
   (b) from about 0.01% to about 0.3% sodium ions;
   (c) from about 0.005% to about 0.08% potassium ions;
   (d) from about 0.1% to about 20% of a carbohydrate which provides
      (i) from about 0.05% to about 10.0% fructose;
      (ii) from about 0.05% to about 10.0% glucose; and
   (e) water.

5. A fluid composition for providing enhanced cellular hydration and drinkability consisting essentially of:
   (a) from about 0.01% to about 0.35% flavanols;
   (b) from about 0.01% to about 0.3% sodium ions;
   (c) from about 0.005% to about 0.08% potassium ions;
   (d) from about 0.1% to about 20% of a carbohydrate which provides
      (i) from about 0.05% to about 10.0% fructose;
      (ii) from about 0.05% to about 10.0% glucose;
   (e) from about 0.001% to about 30% of a flavoring agent;
   (f) from about 0.01% to about 0.04% caffeine; and
   (g) water.

6. A fluid composition for providing enhanced cellular hydration and drinkability consisting essentially of:
   (a) from about 0.01% to about 0.35% flavanols;
   (b) from about 0.01% to about 0.3% sodium ions;
   (c) from about 0.005% to about 0.08% potassium ions;
   (d) from about 0.1% to about 20% of a carbohydrate which provides
      (i) from about 0.05% to about 10.0% fructose;
      (ii) from about 0.05% to about 10.0% glucose;
   (e) from about 0.001% to about 30% of a flavoring agent;
   (f) from about 0.05% to about 0.09% chloride ion; and
   (g) water.

7. A composition according to claim 5 wherein said caffeine concentration is from 0.013% to about 0.03%.

8. A composition according to claim 5 wherein said flavanol concentration is from about 0.02% to about 0.095%.

9. A composition according to claim 8 wherein said flavanol concentration is from about 0.025% to about 0.075%.

10. A composition according to claim 8 wherein said flavanol concentration is from about 0.020% to about 0.095%.

11. A composition according to claim 10 wherein the concentration of flavanols is from about 0.025% to about 0.075%.

12. A composition according to claim 8 wherein said sodium ions are from about 0.02% to about 0.2%, said potassium ions are from about 0.01% to about 0.06%, said carbohydrate is from about 2% to about 10% and wherein said carbohydrate provides from about 1% to about 5% fructose, and from about 1% to about 5% glucose.

13. A composition claim 12 wherein said sodium ions are from about 0.04% to about 0.15%, said potassium ions are from about 0.02% to about 0.04%, said carbohydrate is from about 3% to about 6% and wherein said carbohydrate provides from about 1.5% to about 3% fructose and from about 1.5% to about 3.0% glucose.

14. A composition according to claim 9 wherein said sodium ions are from about 0.02% to about 0.2% said potassium ions are from about 0.01% to about 0.06%, said carbohydrate is from about 2% to about 10% and wherein said carbohydrate provides from about 1% to about 5% fructose, and from about 1% to about 5% glucose.

15. A composition claim 14 wherein said sodium ions are from about 0.04% to about 0.15%, said potassium ions are from about 0.02% to about 0.04%, said carbohydrate is from about 3% to about 6% and wherein said carbohydrate provides about 1.5% to about 3% fructose and from about 1.5% to about 3.0% glucose.

16. A composition according to claim 10 wherein said sodium ions are from about 0.02% to about 0.2%, said potassium ions are from about 0.01% to about 0.06%, said carbohydrate is from about 2% to about 10% and wherein said carbohydrate provides from about 1% to about 5% fructose, and from about 1% to about 5% glucose.

17. A composition claim 16 wherein said sodium ions are from about 0.04% to about 0.15%, said potassium ions are from about 0.02% to about 0.04%, said carbohydrate is from about 3% to about 6% and wherein said carbohydrate provides from about 1.5% to about 3% fructose and from about 1.5% to about 3.0% glucose.

18. A composition according to claim 11 wherein said sodium ions are from about 0.02% to about 0.2% said potassium ions are from about 0.01% to about 0.06%, said carbohydrate is from about 2% to about 10% and wherein said carbohydrate provides from about 1% to about 5% fructose, and from about 1% to about 5% glucose.

19. A composition claim 18 wherein said sodium ions are from about 0.04% to about 0.15%, said potassium ions are from about 0.02% to about 0.04%, said carbohydrate is from about 3% to about 6% and wherein said carbohydrate provides from about 1.5% to about 3% fructose and from about 1.5% to about 3.0% glucose.

* * * * *